US010037409B2

(12) United States Patent
Borden (10) Patent No.: US 10,037,409 B2
(45) Date of Patent: Jul. 31, 2018

(54) AUTOMATED METHOD AND SYSTEM FOR REDUCING THE IMPROPER DISCLOSURE OF DOCUMENTS

(71) Applicant: MRO Corporation, King of Prussia, PA (US)

(72) Inventor: David J. Borden, Merion, PA (US)

(73) Assignee: MRO Corporation, Norristown, PA (US)

( * ) Notice: Subject to any disclaimer, the term of this patent is extended or adjusted under 35 U.S.C. 154(b) by 249 days.

(21) Appl. No.: 14/192,817

(22) Filed: Feb. 27, 2014

(65) Prior Publication Data

US 2014/0244302 A1    Aug. 28, 2014

Related U.S. Application Data

(60) Provisional application No. 61/769,976, filed on Feb. 27, 2013.

(51) Int. Cl.
*G16H 10/60*     (2018.01)
*G06F 19/00*     (2018.01)

(52) U.S. Cl.
CPC ........... *G06F 19/322* (2013.01); *G16H 10/60* (2018.01)

(58) Field of Classification Search
CPC .... G06Q 30/0279; G06Q 20/10; G06Q 40/00; G16H 10/60
USPC ............................................................ 705/3
See application file for complete search history.

(56) References Cited

U.S. PATENT DOCUMENTS

| | | | | |
|---|---|---|---|---|
| 5,664,109 | A | * | 9/1997 | Johnson ................ G06F 19/322 705/2 |
| 5,889,897 | A | * | 3/1999 | Medina .................... G06K 9/03 382/182 |
| 6,453,079 | B1 | * | 9/2002 | McInerny .............. G06K 9/033 382/311 |
| 2006/0129446 | A1 | * | 6/2006 | Ruhl .................. G06F 17/30873 705/306 |

* cited by examiner

*Primary Examiner* — Hiep Van Nguyen
(74) *Attorney, Agent, or Firm* — Lauletta Birnbaum, LLC (57) ABSTRACT

An automated system to reduce improper disclosure of documents containing image information for a patient. The system includes an OCR processing tool that passes each document through an OCR module that converts the document image information into text information, and an automated QC process tool that uses the text information to perform a quality control review for patient demographic matching conditions in the documents.

19 Claims, 7 Drawing Sheets

AUTOMATED METHOD AND SYSTEM FOR REDUCING THE IMPROPER DISCLOSURE OF DOCUMENTS

CROSS-REFERENCE TO RELATED APPLICATIONS

This application claims priority to U.S. Provisional Pat. Application 61/769,976, filed on Feb. 27, 2013.

STATEMENT REGARDING FEDERALLY SPONSORED RESEARCH OR DEVELOPMENT

The present invention was not developed with the use of any Federal Funds, but was developed independently by the inventor.

BACKGROUND

1. Field

The invention relates to a method and system for reducing the improper disclosure of documents, and in particular the invention relates to an automated method and system for reducing the improper disclosure of medical record documents.

2. Background

It is often required to deliver copies of medical records on behalf of hospitals and healthcare providers to third party requesters. Typically, this can be accomplished by electronically importing the copies of the medical records into a document management system before sending them to the requesting party. To comply with privacy laws, regulations, and expectations, the document management system must ensure that no mis-release of medical records occurs; a mis-release occurs when the medical records sent are for the wrong patient.

Typically, the records can be from one to several thousand pages long. It has been found that the risk of a mis-release may be reduced to an acceptable (and extremely small) probability, such as an Improper Disclosure rate of 0.0000335, by checking a sample of the requested documents for pre-information in a manual document quality control (QC) process.

This release of information (ROI) workflow involves a variety of manual processing steps. An error along the way can lead to records being released to the wrong party. Paper and electronic medical record systems can occasionally contain misfiled documents. Even if the correct patient folder, paper or electronic, is accessed, that folder can contain documents for the wrong patient. In addition, the typical operational processing of patient records, i.e., filing, re-filing, copying, printing, and the like, can create concatenated records of two or more patients.

The Manual Document QC process involves the use of trained staff (hereinafter referred to as a QC'er) that reviews each request before it is delivered to the requesting party during the ROI workflow. The QC'er is presented on a computer screen with the first five and last five pages imported into the ROI system as a sample, along with the patient's First and Last Name, and their Date of Birth (DOB), Medical Record Number (MRN), and Social Security Number (SSN), if available.

The QC'er checks to make sure that the following Patient Demographic Matching Conditions are all true: the patient First and Last Name are present on at least one of the first 5 pages; the patient First and Last Name are present on at least one of the last 5 pages; and at least one of the following elements: DOB, MRN, or SSN; is present somewhere in the total 10 pages (first 5 and last 5).

If these conditions are not met, the request is put on hold, and the records are not delivered until other staff can confirm that the documents are for the correct patient.

While this solution works well for quality of service, it is labor intensive. Thus, there exists the need for a new technology based automated process for improving the efficiency, as well as increasing the sampling size so that a larger sample or all pages can be inspected to even further decrease the risk of a mis-release.

SUMMARY

An automated system to reduce improper disclosure of documents containing image information for a patient. The system includes an OCR processing tool that passes each document through an OCR module that converts the document image information into text information, and an automated QC process tool that uses the text information to perform a quality control review for patient demographic matching conditions in the documents.

The automated QC process tool may determine whether each page of each document can be positively identified with the patient, if the document is positively identified then the document is released. If the document is not positively identified, then the QC process tool may scan for improper patient identifiers. A QC assist process tool may be provided that provides side by side comparison of requested document information with the text information. The QC assist process tool further comprises a "heat map" of the document coded based on an amount of errors contained in the documents which facilitates the operator to quickly view only documents exceeding a predefined threshold.

BRIEF DESCRIPTION OF THE DRAWINGS

The embodiments will be described in detail with reference to the following drawings in which like reference numerals refer to like elements wherein.

DETAILED DESCRIPTION

The Automated Method and System for Reducing the Improper Disclosure of Documents Quality Control (QC) Process of the present invention provides the following additional capabilities over existing systems: enhancements to the ability to match patient identifying information in the original request to the patient identifying information taken from the requester (this information is typically keyed in when the request is first logged) and the elimination of the need to review documents that clearly belong to the correct patient. This allows the expansion of the scope of images normally checked; and, permits the "needle in the haystack" to be found using heuristic algorithms by analyzing thousands images of records in real time.

The system provides three tools: an OCR Processing tool, an automated QC Process Tool, and a QC Assist Tool. The OCR Processing tool passes each document image through an optical character recognition (OCR) module that converts the image information into text information. Typically, over 500,000 images may be processed each day with the OCR module. In contrast, in existing manual processes, approximately 10,250 pages could be viewed each day during the QC process (215,000 per month). The automated QC Process tool determines whether each page of the record can be positively identified with the patient. If this is the case, then a manual QC process is likely not required. In addition, the automated QC Process tool scans for improper patient identifiers, i.e., the needle in the haystack, to immediately cease further document processing. The QC Assist Process Tool provides side by side comparison of requested document information with the information keyed. A "heat map" of the entire document is also provided which facilitates the operator to quickly view only suspect documents.

Figure 1:
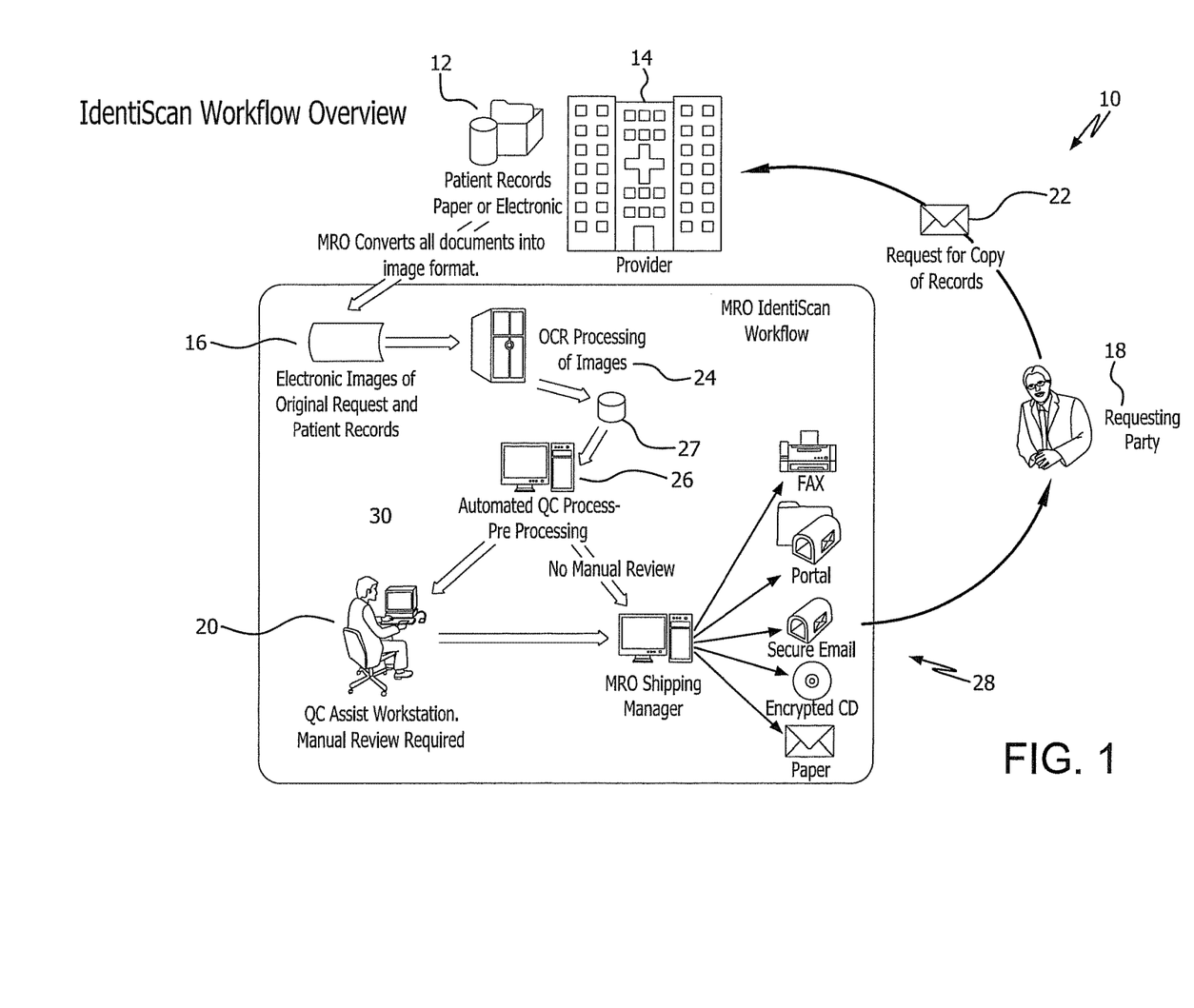
FIG. 1 is a schematic overview of the Automated Method and System for Reducing the Improper Disclosure of Documents in accordance with the present invention.

Referring now to FIG. 1, the invention relates to an Automated Method and System for Reducing the Improper Disclosure of Documents 10. System 10 is used to deliver electronic copies of original medical records 12 on behalf of hospitals and healthcare providers 14 to third party requesters 18 such as lawyers, insurance companies, record retrieval services and government agencies. The electronic record copies 16 are electronically imported by converting the documents into an image format into the system 10 before sending the record copies 16 to the third party requesters 18.

When the records 16 are ready to be delivered, they are OCR'd by an automated OCR Server 24. The resulting OCR data is stored on a server 27, for use by the automated QC Process of the present invention. A second automated server, an automated QC Process server 26, uses the OCR data to perform a quality control review that is similar to that performed by operators in the Manual QC Process. The automated QC process server conducts a review for the Patient Demographic Matching conditions, described in greater detail below, in the sample of documents being reviewed. This automated check alone, can successfully validate about 70% of the requests 22, to the same level of accuracy as the existing Manual QC Process.

The system 10 also includes additional tools, described in greater detail below, that increase the accuracy of the quality control review. For example, a tool may be provided that facilitates the spot checking of requests that fail the Auto-QC Server 26 review. In addition, the matching algorithms may be tuned and refined to increase their accuracy, for example by adding new Date formats for checking the Date of Birth and/or adding new rules for matching such things as Hyphenated or Double First and Last Names.

The system also permits the manual spot checking of requests that pass the process, to make sure that false positive matches are not being made. If excessive false positives are seen, the process can be further tuned to balance between achieving a high-percentage of automation vs. not letting mis-releases slip through because of false matching.

The system 10, also allows the records providers 14 to determine the sampling rate. For instance, the system 10 could sample the first 10, last 10, and some 10 pages in the middle. Alternatively, the system could perform Patient Matching on all pages, and set a threshold for an acceptable number of pages that match. Other sampling rate thresholds are also contemplated by the presented invention.

Figure 2:
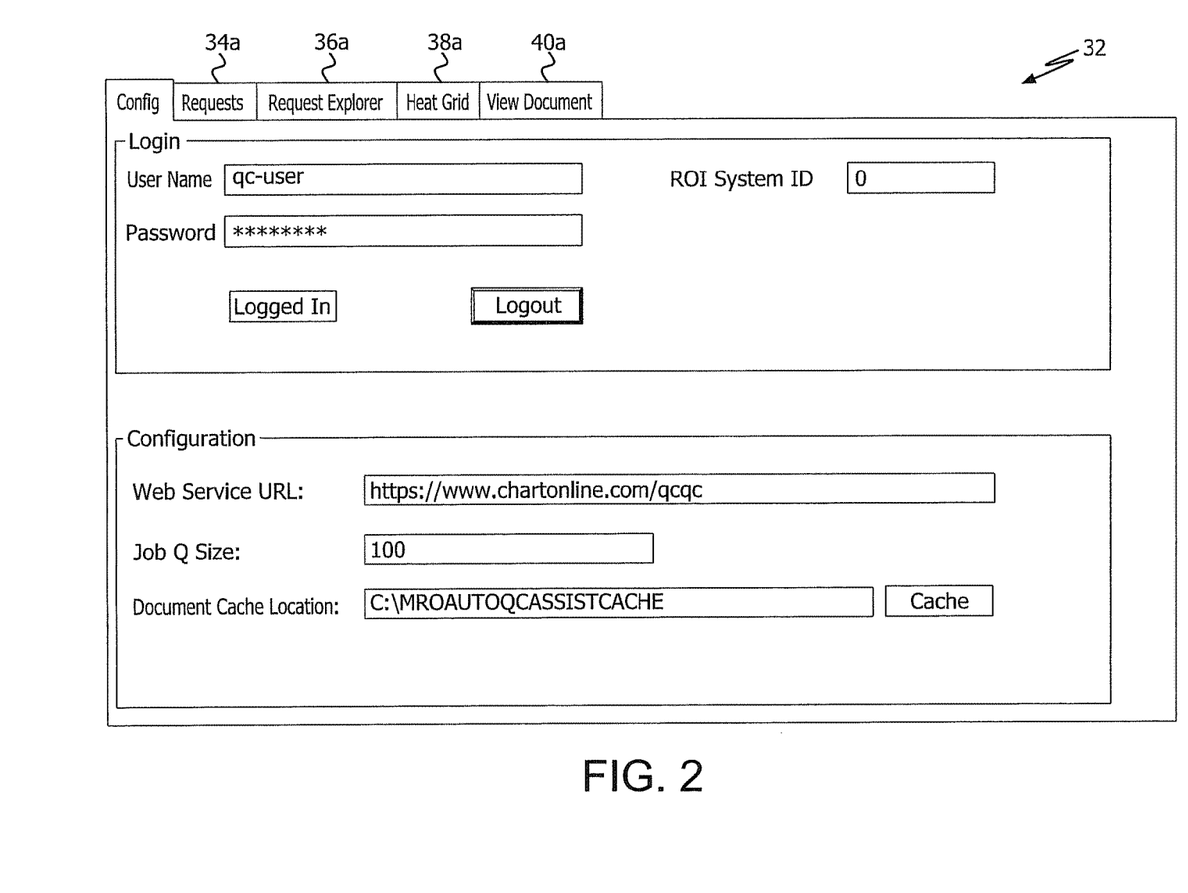
FIG. 2 is a screenshot of the Login/Configuration screen of the method and system of FIG. 1.

Requests that fail the Auto-QC Server 26 process are looked at manually by Document QC staff 20 during a manual review process. The third component of the QC Process 10 is a tool 30 for Document QC staff 20 that is illustrated in the screenshots shown in FIGS. 2-6. The tool includes a login/configuration screen 32 shown in FIG. 2, a request review screen 34 shown in FIG. 3, a request explore screen 36 shown in FIG. 4, a heat grid screen 38 shown in FIG. 5, and a view document screen 40 shown in FIG. 6.

Once the user has logged into the system using the login screen 32 of the QC Assist tool 30, the user may select tabs corresponding to the screen the user desires to view. A tab 34a is provided to display the request review screen 34 shown in FIG. 3. A tab 36a is provided to display the request explore screen 36 shown in FIG. 4. A tab 38a is provided to display the heat grid screen 38 shown in FIG. 5. And, a tab 40a is provided to display the view document screen 40 shown in FIG. 6. Each screen will be described in greater detail below.

Figure 3:
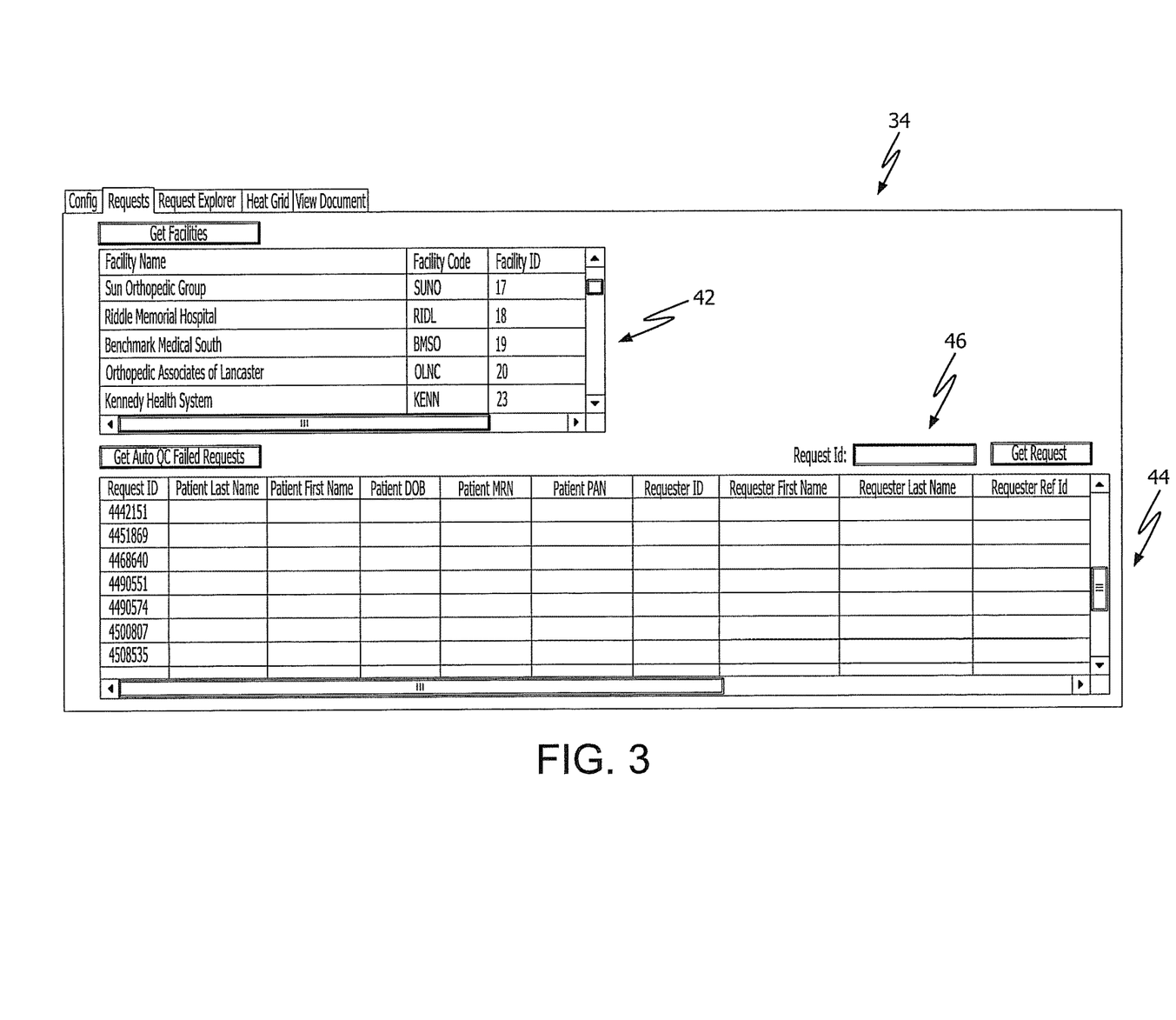
FIG. 3 is a screenshot of the Request screen of the method and system of FIG. 1.

Referring to FIG. 3, the review screen 34 provides the user with a display to review requests 22 for each provider 14 in section 42 or according to the requests 22 that have not passed the automatic review process 26 in section 44. The user may also select a particular request by entering a request ID into search box 46. Selecting a particular facility displays the Failed Results which have to be reviewed. If the request number is known, the user can use the Request ID search box 46 to display a particular request.

The user reviews the requests 22 that need further review on screen 34. Once the user selects a specific request, the user is taken to or may select the request review explorer screen 36 shown in FIG. 4.

Figure 4:
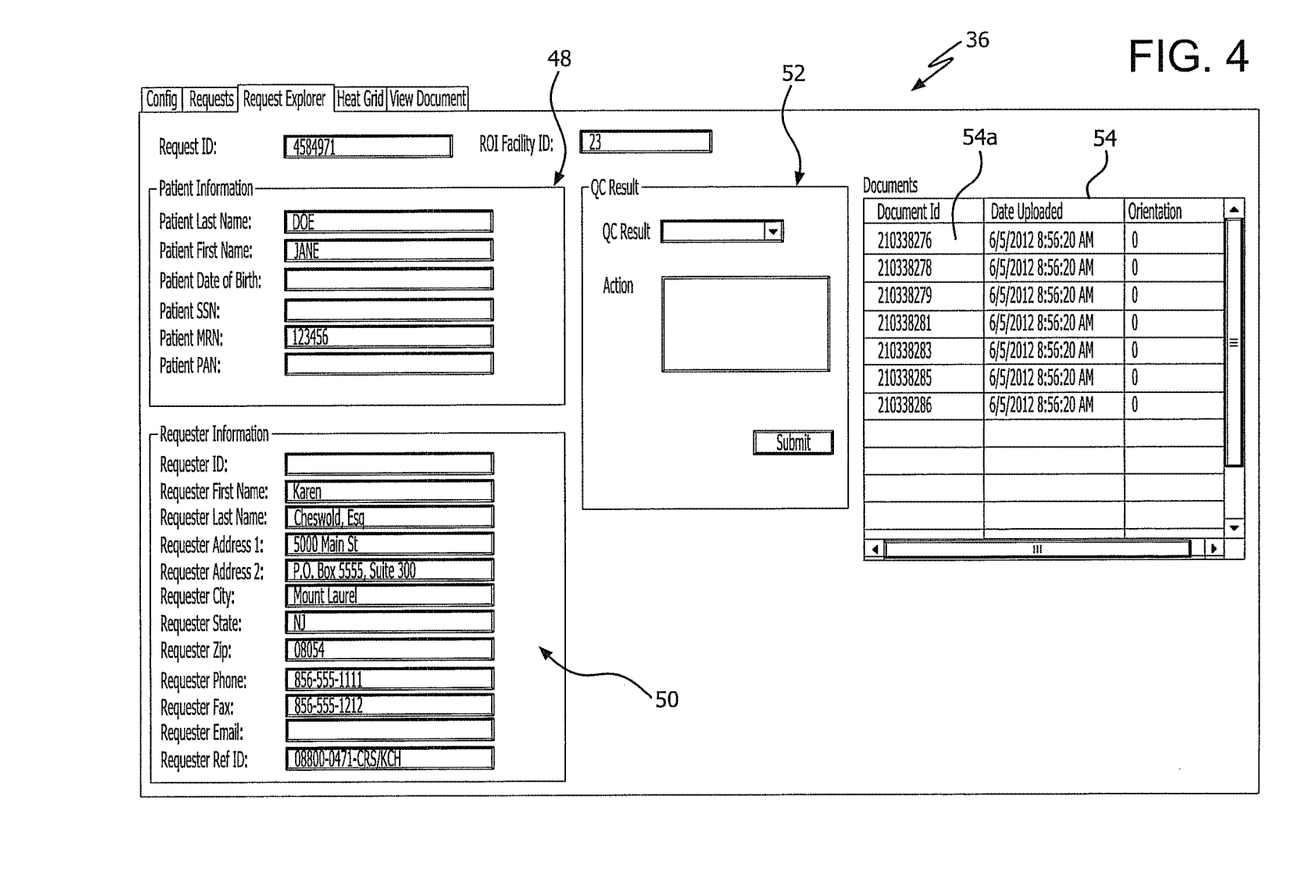
FIG. 4 is a screenshot of the Request Explorer screen of the method and system of FIG. 1.

The review explorer screen 36 is used for troubleshooting and presents the user with patient data 48, requester data 50, the QC result 52. The result 52 is based on whether the request can be Passed or has to be Failed based on the accuracy of the patient demographics. In the manual QC process, this result is determined by the user. and a list of documents 54 contained in the request 22 which may be reviewed. Selecting a specific document, such as document 54a, or documents brings the user to the view document screen 40 of FIG. 6, as described in greater detail below.

Figure 5:
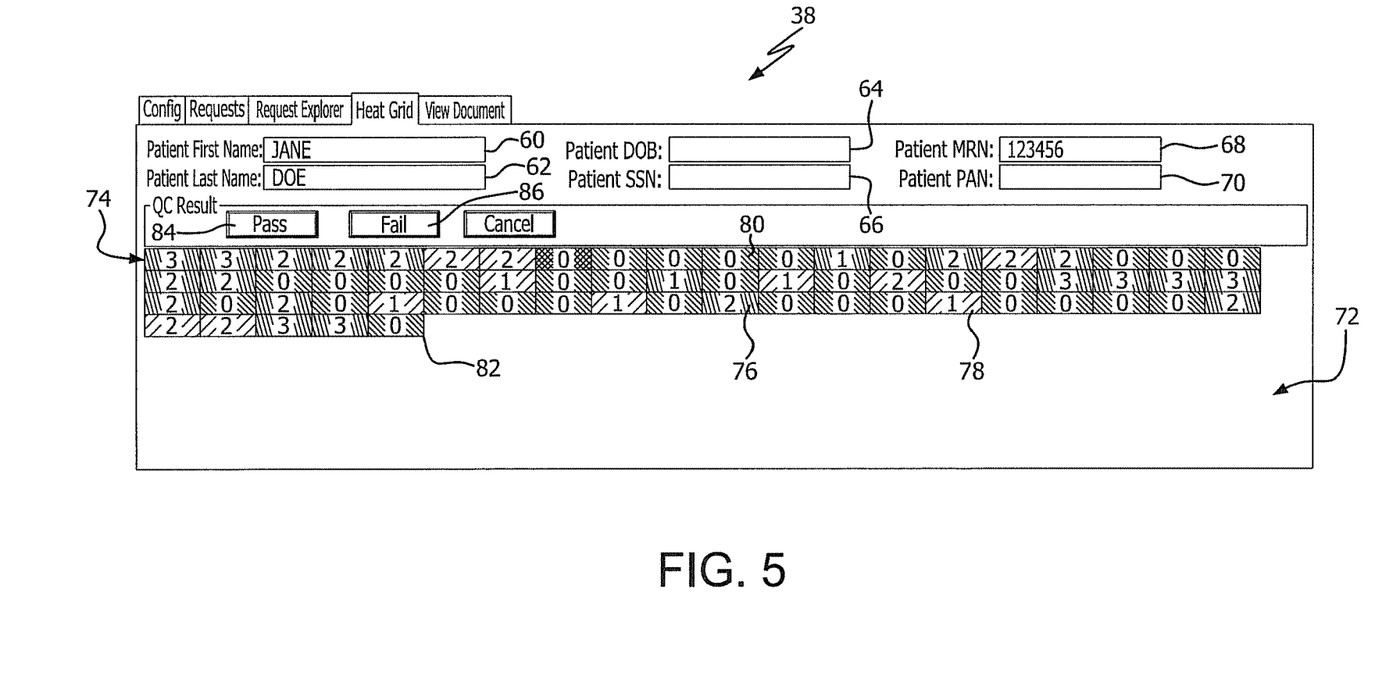
FIG. 5 is a screenshot of the Heat Grid screen of the method and system of FIG. 1.

Referring now to FIG. 5, the QC Assist tool 30 also presents a high-level view of each set of documents in a color-coded grid or "heat grid" in screen 38. Typically, the user accesses the QC Assist tool by clicking the Heat Grid View button from the Request Status screen. The heat grid screen 38 displays the number and quality of Patient Demographic Matches for each document in the document set.

The Heat Grid screen 38 displays patient identifying data from the documents being reviewed. For example, the Patient First Name 60, Patient Last Name 62, Patient Date of Birth 64, Patient Social Security Number 66, Patient Medical Record Number 68, and the Patient Account Number 70.

The Heat Grid screen 38 also displays a Heat Grid Section 72. The Heat Grid Section 72 shows a visual representation of the quality of the matches of the documents contained in the particular request under review. Heat Grid Section 72 contains a square or rectangle 74 corresponding to each document. It should be understood that other shapes are suitable and within the scope of the present invention. Each Square 74 is colored or otherwise differentiated to represent the quality of the match of the document. The Red grid squares 80 represent no matches. It should be understood, that the system requirements for what is required for a match can be adjusted as the program evolves. Green grid squares 76 signify two or more matches (Name, DOB, MRN, SSN). Yellow grid squares 78 represent only one match. In addition, the number of matches may also be provided in each grid square as shown to further aid the reviewer. This condensed and colored grid allows the QC reviewer to see patterns of matching and non-matching documents, along with a zoom-view panel to allow quick inspection of any page or sequence of pages that has a low Patient Matching rating. The user may look at any page desired by selecting a particular grid square, for example grid square 82, which will take the reviewer to View Document screen 40 to view the particular document. Selection buttons are also provided so that the reviewer may indicate a Pass 84 or a Fail 86 validation decision for the set of documents under review.

Figure 6:
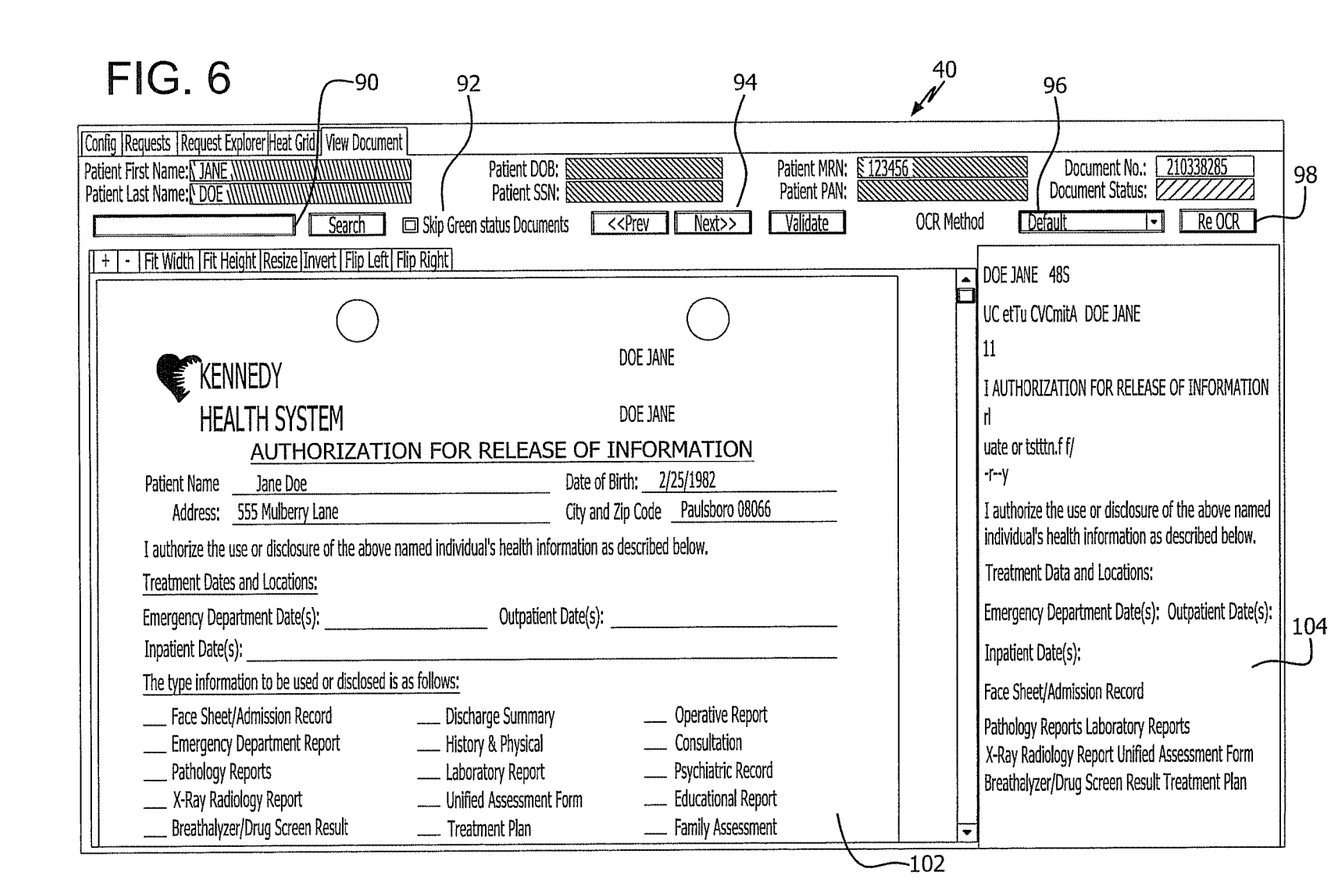
FIG. 6 is a screenshot of the View Document screen of the method and system of FIG. 1.

Referring now to FIG. 6, the view document screen 40 is shown. This screen permits the user to view any document in a document request set under review. The view document screen 40 provides a search box 90 for searching for specific text contained in the document. A box 92 is provided which permits the user to select to skip documents that have successfully passed view, i.e., Green status documents, during navigation. Page navigation selectors 94 are provided that permit the user to quickly navigate through the documents. The user may also select the OCR method being used by selecting button 96 in order to increase the likelihood of a match between the patient demographics logged and the text which was searched by OCR for increased accuracy. Button 98 is also provided to permit the user to reOCR the document using the selected OCR method. The user may also manually validate the document by selecting validation button 100 or reject the document. The validate button also serves as a page counter for the QC'er to know how many pages they have looked at in the request. For example, pages can be color-coded "blue" pages for those that were "validated" as shown in FIG. 5. The image 102 of the document is also provided as well as the OCR text 104 for the document in the view document screen 40.

Most medical record document sets are spotty with large numbers of green or yellow grid squares, and a few patches of red, typically due to the presence of handwritten documents or run-on forms that only have the patient information on the first page, and the like.

QC Assist tool 30 allows the QC'er the ability to quickly and easily select the patches of red and Zoom-View the associated documents, and validate them, as described above. The validation of a document, along with the date and validating user ID is saved on the server for later auditing.

After the automated QC Process Pre-Processing and the manual QC process, if needed, the record copies 16 can be released 28 for shipping to the requesting party 18 through any suitable delivery mechanism, such as via physical mailing, shipping of an encrypted CD, Secure Email, an Electronic or Web Portal, fax, and the like.

Figure 7:
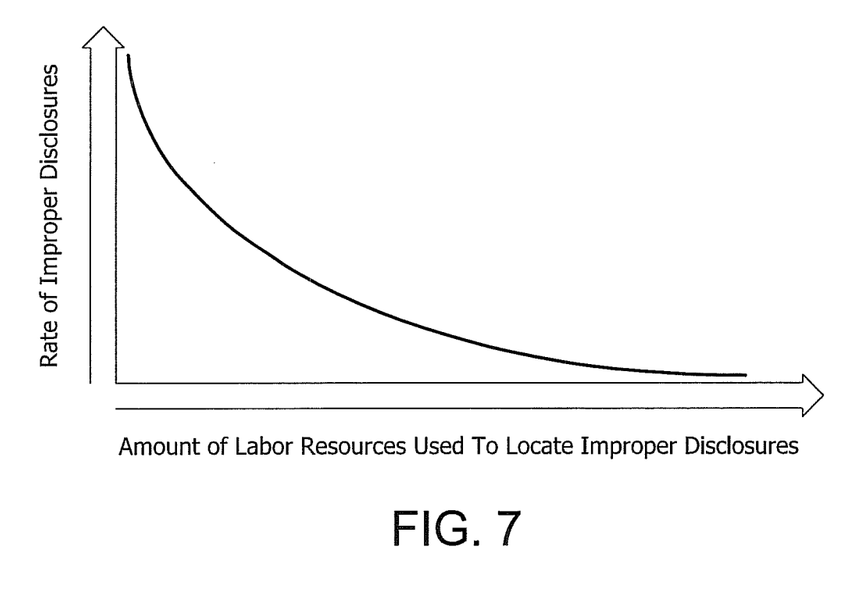
FIG. 7 is a graph of the rate of improper disclosures vs the resources expended to locate improper disclosures of the method and system of FIG. 1.

The tool 30 may also be used to quickly look at and validate all red pages. For example, all pages in the request set may be validated. Alternately, the tool may be used to present the QC'er with only those pages for which good Patient Demographic matching conditions were not found, thus cutting labor costs while still ensure that we are inspecting every page that is delivered, as shown in the Graph of FIG. 7.

In addition to allowing the QC Staff to complete the review of requests, the QC Assist program provides a powerful spot-checking tool, allowing QC Process managers the ability to spot check requests at will for those requests that were passed on by the Auto-QC Process Server, to make sure that it is not creating false-positives; those requests that were passed on by the QC'ers to ensure they are doing their job properly; and to retrospectively inspect requests that were found to have been mis-released, to understand why the system failed to catch it, and use this information to tune the system's matching algorithms (or other processes that may have broken down)

The system 10 permits the tuning of the OCR process over time to increase the ability to OCR information contained in the files. Because the OCR process is costly in terms of time and computer processing resources, an initial OCR may be done with generic parameters that are selected to produce the best overall results for an average document. For those documents that fail the Automated QC Process, the documents can be taken that had no Patient Demographic matches and further work to OCR them may be performed, such as trying different OCR methods, different orientation of the image, different zoning parameters, or other methods to try to extract more OCR data from the image.

The QC Matching algorithms are tuned over time. Using the QC Assist tool, software designers can see places where the matching could be increased by Allowing matches of alternative "common OCR error" substitutions. For instance, OCR may read: "10/25/1964" as "10|125!1964". If "|" or "l" is substituted for "/" in a date match, the matching efficiency can be increased. However, using substitutions to increase matching efficiency comes at the cost of potential false positives. This has to be balanced, through two methods: 1) using a different color coding on the Head Grid to indicate a "substituted" match; and 2) building into the overall document set QC algorithm an allowance for some ratio of substituted matches to "hard" or un-substituted matches.

Another problem is that certain forms may lend themselves to false positives. For instance, if a Medical Facility in North Carolina has the words "North Carolina" on their forms, a patient named "Carol" would be matched by Carolina. The system permits the addition of rules about the proximity of first and last name to reduce this type of problem.

As developers use the QC Assist tool to spot check requests, more and more intelligence about tuning to the various algorithms are acquired, and this knowledge is used to refine the process further.

Although embodiments have been described with reference to a number of illustrative embodiments thereof, it should be understood that numerous other modifications and embodiments can be devised by those skilled in the art that will fall within the spirit and scope of the principles of this disclosure. More particularly, various variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

What is claimed is:

1. An automated system to reduce improper disclosure of documents containing a plurality of image pages of image information for a patient, comprising:

an optical character recognition (OCR) processing tool that passes each document through an OCR module that converts a predetermined number of pages of the document image information into text information, wherein the predetermined number of OCR'ed pages is less than all the pages for at least one sampled document; and an automated quality control (QC) process tool that uses the text information to perform a review for patient demographic matching conditions in the documents, wherein the automated QC process tool determines whether a predetermined number of pages of each document can be positively identified with the patient, if the document exceeds a predetermined threshold of positively identified pages, then the document is released to deliver to a requester of the document;

a QC assist process tool that receives documents that fail the QC process tool test for review and validation by a document reviewer, the QC assist process tool comprises a "heat map" for each failed document, a visual representation of each page of the failed document is displayed and each page of the failed document is visually coded based on an amount of matches of patient demographic information received from a requester of the documents to patient demographic matching conditions in the text information for that page which facilitates the reviewer to quickly view only failed documents and validate documents containing a sufficient number of matches for release to deliver to the requester.

2. The automated system to reduce improper disclosure of documents, according to claim 1, wherein if each page of the document is not positively identified, then the QC process tool scans for improper patient identifiers that do not match the patient's identifiers, if found the QC process is terminated.

3. The automated system to reduce improper disclosure of documents, according to claim 2, wherein the QC assist process tool provides side by side comparison of requested document information with the text information only if the predetermined threshold of positively identified pages is not met.

4. The automated system to reduce improper disclosure of documents, according to claim 3, "heat map" of the document coded is based on an amount of errors contained in the documents which facilitates the operator to quickly view only documents exceeding a predefined threshold.

5. The automated system to reduce improper disclosure of documents, according to claim 1, wherein the QC assist process tool provides side by side comparison of requested document information with the text information only if the predetermined threshold of positively identified pages is not met.

6. The automated system to reduce improper disclosure of documents, according to claim 5, wherein the "heat map" of the document coded is based on an amount of errors contained in the documents which facilitates the operator to quickly view only documents exceeding a predefined threshold.

7. A system to reduce improper disclosure of documents from a provider of the documents to a requester of the documents, comprising:

a tool that imports electronic copies of the documents, the documents contain one or more image pages of image information for a patient;

an optical character recognition (OCR) processing tool that passes each copied document through an OCR module that converts the copied document image information into text information;

an automated quality control (QC) process tool that compares patient identifying information received from a requester of the documents to patient demographic matching conditions in the text information of the copied documents, wherein the automated QC process tool tests whether each copied document can be positively identified with a patient, copied documents that pass the test are released to deliver to the requester; and a QC assist process tool that receives copied documents that fail the QC process tool test for review and validation by a document reviewer, the QC assist process tool comprises a "heat map" for each failed document, a visual representation of each page of the failed document is displayed and each page of the failed document is visually coded based on an amount of matches of patient identifying information received from a requester of the documents to patient demographic matching conditions in the text information for that page which facilitates the reviewer to quickly view only failed documents and validate documents containing a sufficient number of matches for release to deliver to the requester.

8. The system to reduce improper disclosure of documents from a provider of the documents to a requester of the documents according to claim 7, wherein the visual representation of each page of the failed document is visually coded based if the reviewer has validated the page.

9. The system to reduce improper disclosure of documents from a provider of the documents to a requester of the documents according to claim 8, wherein the visual representation of each page of the failed document displays the number of matches contained in that page.

10. The system to reduce improper disclosure of documents from a provider of the documents to a requester of the documents according to claim 9, wherein the visual coding comprises a first visual coding for no matches, a second visual coding for one match, a third visual coding for more than one match, and a fourth visual coding for the validated page.

11. The system to reduce improper disclosure of documents from a provider of the documents to a requester of the documents according to claim 10, wherein QC assist process tool provides a plurality of OCR methods for the reviewer may run on selected failed documents.

12. The system to reduce improper disclosure of documents from a provider of the documents to a requester of the documents according to claim 11, wherein the visual representations have a rectangular or square shape and are presented in a grid format of rows and columns of visual representations to facilitate the display of patterns in matching and non-matching pages.

13. The system to reduce improper disclosure of documents from a provider of the documents to a requester of the documents according to claim 12, wherein the QC assist process tool comprises a viewer to display pages or sequences of pages by selecting the desired visual representations.

14. The system to reduce improper disclosure of documents from a provider of the documents to a requester of the documents according to claim 13 wherein the QC assist process tool provides side by side manual comparison of the patient identifying information received from the requester to the patient demographic matching conditions in the text information for a page.

15. The system to reduce improper disclosure of documents from a provider of the documents to a requester of the documents according to claim 7, wherein the visual representation of each page of the failed document displays the number of matches contained in that page.

16. The system to reduce improper disclosure of documents from a provider of the documents to a requester of the documents according to claim 7, wherein the visual coding comprises a first visual coding for no matches, a second visual coding for one match, a third visual coding for more than one match, and a fourth visual coding for the validated page.

17. The system to reduce improper disclosure of documents from a provider of the documents to a requester of the documents according to claim 7, wherein QC assist process tool provides a plurality of OCR methods for the reviewer may run on selected failed documents.

18. The system to reduce improper disclosure of documents from a provider of the documents to a requester of the documents according to claim 7, wherein the visual representations have a rectangular or square shape and are presented in a grid format of rows and columns of visual representations to facilitate the display of patterns in matching and non-matching pages.

19. The system to reduce improper disclosure of documents from a provider of the documents to a requester of the documents according to claim 7, wherein the QC assist process tool comprises a viewer to display pages or sequences of pages by selecting the desired visual representations.

* * * * *